(12) United States Patent
Modi

(10) Patent No.: US 8,728,448 B2
(45) Date of Patent: May 20, 2014

(54) USE OF AGGLOMERATED HYDROXYETHYLCELLULOSE IN PHARMACEUTICAL, PERSONAL CARE AND HOUSEHOLD CARE APPLICATIONS

(75) Inventor: Jashawant J. Modi, Hockessin, DE (US)

(73) Assignee: Hercules Incorporated, Wilmington, DE (US)

( * ) Notice: Subject to any disclaimer, the term of this patent is extended or adjusted under 35 U.S.C. 154(b) by 1226 days.

(21) Appl. No.: 12/008,217

(22) Filed: Jan. 9, 2008

(65) Prior Publication Data

US 2008/0166311 A1 Jul. 10, 2008

Related U.S. Application Data

(60) Provisional application No. 60/879,855, filed on Jan. 10, 2007.

(51) Int. Cl.
*A61K 8/00* (2006.01)
*A61K 47/00* (2006.01)
*A61K 8/18* (2006.01)
*A61Q 19/10* (2006.01)

(52) U.S. Cl.
USPC ........... 424/70.1; 514/781; 510/119; 510/130

(58) Field of Classification Search
USPC .................. 424/70.1; 514/781; 510/119, 130
See application file for complete search history.

(56) References Cited

U.S. PATENT DOCUMENTS

| 4,886,660 A | * | 12/1989 | Patel et al. ................. 424/70.13 |
| 5,869,029 A | | 2/1999 | Graff-Andersen et al. ..... 424/52 |
| 6,258,342 B1 | * | 7/2001 | Harcum et al. ................. 424/49 |
| 2003/0099702 A1 | | 5/2003 | Staniforth et al. ............ 424/465 |

FOREIGN PATENT DOCUMENTS

| WO | WO 01/32132 A2 | 4/2001 | ............... A61K 7/00 |
| WO | WO 03/072084 A1 | 9/2003 | ............... A61K 9/20 |
| WO | WO 2006/088963 A1 | 8/2006 | ............. C07F 9/145 |
| WO | WO 2007/089834 A2 | 8/2007 | |

OTHER PUBLICATIONS

Hercules, Natrosol 250 Product Data, Jul. 2005, p. 1-2.*
EP 0 572 768 (Lorenz) 1993 [online] [retrieved on May 9, 2010]. Retrieved from EPO Database.*

* cited by examiner

*Primary Examiner* — Blessing M Fubara
*Assistant Examiner* — Jennifer A Berrios
(74) *Attorney, Agent, or Firm* — Shaorong Chen; Joanne Rossi; Michael Herman

(57) ABSTRACT

The present invention is related to the use of glyoxal-free compositions, more particularly, to the use of hydroxyethylcellulose agglomerated with low molecular weight hydroxyethylcellulose in consumer products, in particular, pharmaceutical, personal care (excluding oral care compositions), as well as household care applications.

11 Claims, 6 Drawing Sheets

USE OF AGGLOMERATED
HYDROXYETHYLCELLULOSE IN
PHARMACEUTICAL, PERSONAL CARE AND
HOUSEHOLD CARE APPLICATIONS

RELATED APPLICATIONS

This application claims the benefit of U.S. Provisional Application Ser. No. 60/879,855, filed on Jan. 10, 2007, which is incorporated herein by reference in its entirety.

FIELD OF INVENTION

The present invention is related to a polysaccharide composition and more particularly, to hydroxyethylcellulose compositions which when applied in water are capable of exceptional dispersion, minimum lump formation and very quick hydration to reach maximum desired viscosity. The invention concerns use of hydroxyethylcellulose compositions in consumer products, in particular, pharmaceutical, personal care (excluding oral care compositions), as well as household care applications.

BACKGROUND OF THE INVENTION

It is well known in the consumer products such as pharmaceutical, personal care (excluding oral care compositions), as well as household care applications to formulate products that provide useful characteristics such as cleansing, cleaning protecting, and benefiting, depositing and moisturizing, and firming, conditioning, providing occlusive barriers, tinting and providing emolliency. In these consumer products water-soluble polymers are used as rheology modifiers for the final compositions. Polysaccharide derivatives such as cellulose ethers, and polygalactomannan and polygalactomannan derivative products are among the best known polysaccharides for use as rheology modifiers in these applications.

Water-soluble polymers are heavily used in a variety of consumer products. Despite their environmentally friendly and biodegradable advantages, they suffer from the tendency to form lumps when in contact with water and take much longer to dissolve. Dissolution, by definition, is a loosely used term. In this case, dissolution is used to represent the two steps by which polymers go into aqueous solutions. In the first step, the polymer is dispersed into the aqueous solution. The time it takes the polymer to disperse is subject to a good deal of variability. Dispersion could be as short as few seconds or as long as several hours depending on technique, instrumentation, morphology and surface chemistry of the polymer. After the polymer is dispersed, the polymer undergoes a hydration step. In this step, polymer chains loosen up and expand their hydrodynamic volume occupying the whole solution and building up viscosity on the way. As soon as polymer molecules contact water, they tend to swell very quickly and get in contact with neighboring particles. They glue together and form lumps of various sizes that tend to delay their hydration time significantly. Good dispersion is a prerequisite for minimal lump formation and ultimately quick hydration in final applications. In all systems of water-soluble polymers, lump formation is considered a rate determining step for total dissolution time.

U.S. Pat. No. 5,869,029 discloses compositions comprising water-soluble or water-swellable polymers agglomerated by treatment with polyols, and the use of these compositions in making toothpastes. The polyols of use in this composition are selected from the group consisting of sugar alcohols, glycerol, polyethylene glycol, propylene glycol, and mixtures thereof. This composition is of utility for producing toothpaste formulations.

U.S. Pat. No. 6,258,342 discloses the use of water or aqueous polymers agglomerated water-soluble or water-swellable polymer in oral care compositions. The oral care composition or dentifrice described in this patent contains abrasives, humectants, and water-soluble polymers.

In consumer products and especially in the personal care industry, there is a safety concern regarding presence glyoxal in formulation ingredients. Currently many hydroxyethylcellulose products (HEC) such as (Natrosol HEC, available from Hercules Incorporated) and hydrophobically modified hydroxyethylcellulose products (HMHEC) (Polysurf® 67 HMHEC available from Hercules Incorporated) are surface treated with glyoxal for ease dispersion by formulators. Glyoxal-free easily dispersable polymers offer an opportunity of easily incorporating these materials into consumer product formulations for use in personal care and, household care applications where there are concerns regarding the presence of glyoxal in the formulations.

SUMMARY OF THE INVENTION

The present invention relates to a composition of agglomerated hydroxyethylcellulose wherein a cellulose ether, more particularly a hydroxyethylcellulose, is used as an agglomerating agent.

This invention further is directed to the process for preparing the agglomerated hydroxyethylcellulose compositions mentioned above.

This invention is further directed to functional use of agglomerated hydroxyethylcellulose compositions in consumer products such as pharmaceutical, household care and personal care (excluding oral care) compositions. The consumer product comprising a) an agglomerated hydroxyethylcellulose composition, b) a consumer product active ingredient material, and c) water, wherein the agglomerated hydroxethylcellulose composition comprises a particulate hydroxyethylcellulose and a low molecular weight hydroxyethylcellulose composition.

BRIEF DESCRIPTION OF THE FIGURES

FIG. 4 contains duplicate tests.

DETAILED DESCRIPTION OF THE INVENTION

Figure 1:
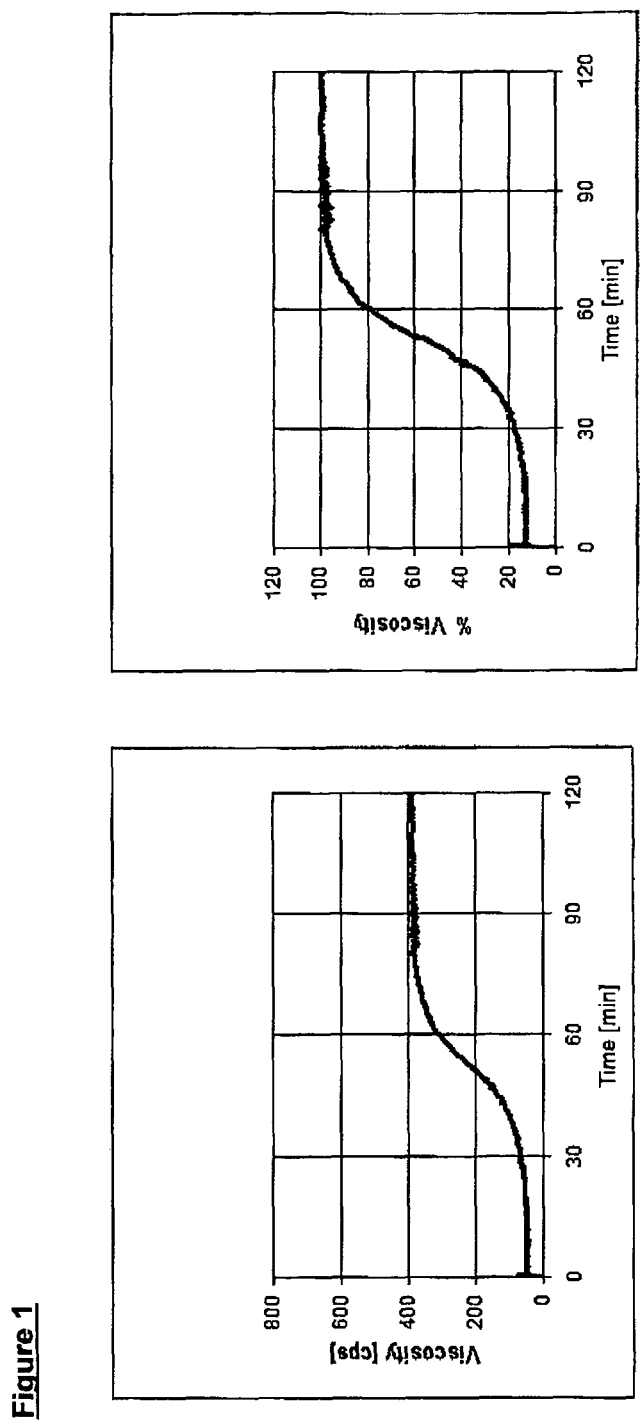
FIGS. 1 and 2 each contain a plot of the viscosity in centipoise (cps) over time, as measured using a Haake Model VT501 viscometer, as well as a plot of the percentage viscosity at given time based on the final viscosity of Comparative Example 1.

In the consumer products industry, especially in the personal care industry, there is a safety concern regarding presence glyoxal in the formulation ingredients. Currently many hydroxyethylcellulose products (HEC) (Natrosol® HEC, available from Hercules Incorporated) and hydrophobically modified hydroxyethylcellulose products (HMHEC) (Polysurf® 67 HMHEC available from Hercules Incorporated) are surface treated with glyoxal to make them easily dispersable in aqueous solutions by formulators. Glyoxal-free easily dispersable polymers offer an opportunity to easily incorporate these materials into consumer products such as personal care (excluding oral care compositions), pharmaceutical or household care uses.

Agglomeration is defined herein as the aggregation of individual particles resulting in an increase in the particle size of the particulate material.

Agglomerated HEC material of use in the present invention may be made by the process of agglomerating as described in U.S. Pat. No. 6,258,342, incorporated herein by reference in its entirety. Agglomerated HEC material of use in the present invention may be prepared by spraying a particulate HEC with an aqueous solution of HEC, preferably a low molecular weight HEC. The low molecular weigh being defined as a HEC with a lower molecular weight than the particulate HEC. A preferred low molecular weight HEC is exhibits a viscosity in a 2% aqueous solution of less than approximately 350 cps, preferably approximately 15 cps. Commercially available fluidized bed spray units may be employed for this agglomeration operation.

Samples of the agglomerated HEC material of use in the invention (Natrosol® 250HHX-GF HEC) were evaluated to determine their dispersion, hydration and dissolution properties.

The HEC was agglomerated with 5% of a low molecular weight HEC (low viscosity HEC aqueous solution (Natrosol® L HEC available from Hercules Incorporated)) in a fluid bed dryer. A sieved sample of the agglomerated HEC composition in particle size range 400-800 micron was tested.

The consumer product of the present invention comprise an agglomerated HEC composition, a consumer product active ingredient material, and an amount of water.

Examples of the consumer product active ingredient materials include sun ray (UV) absorbers, sun screen agents, moisturizers, humectants, benefiting agents for hair, skin, nails, depositing agents such as surfactants and polysaccharide polymers, occlusive agents, moisture barriers, lubricants, emollients, anti-aging agents, antistatic agents, abrasive, antimicrobial agents, insect repellent agents, drug delivery agents, secondary conditioners, exfoliants, lustering agents, tanning agents, luminescent, colors, anti-odorizing agents, fragrances, viscosifying agents, salts, lipids, phospholipids, hydrophobic plant extracts, vitamins, foam stabilizers, pH modifiers, preservatives, suspending agents, silicone oils, silicone derivatives, essential oils, oils, fats, fatty acids, fatty acid esters, fatty alcohols, waxes, polyols, hydrocarbons, dust collectors, polishing agents, stain removing agents, anti-redeposition agents, coloring agents, tinting agents, scrubbing agents, benefiting agents for wood, tiles, and other hard surfaces, automobile treatment agents.

The following examples will serve to illustrate the invention, parts and percentages being by weight unless otherwise indicated.

EXAMPLES

Dispersion Properties with Haake Viscometer Test

Samples were studied for their dispersion (lumping/no lumping), hydration and dissolution properties with a Haake Model VT501 viscometer. All tests were run in deionized water at 25° C., 300 rpm using FL10 sensor.

Figure 2:
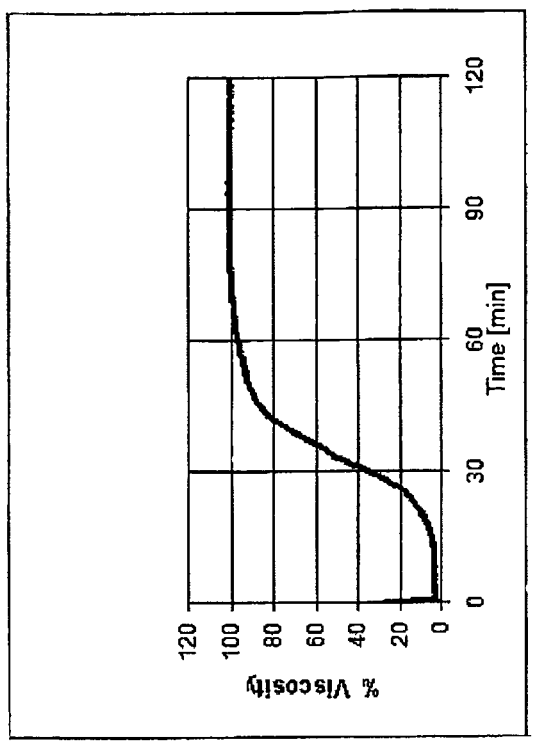
Figure 2:
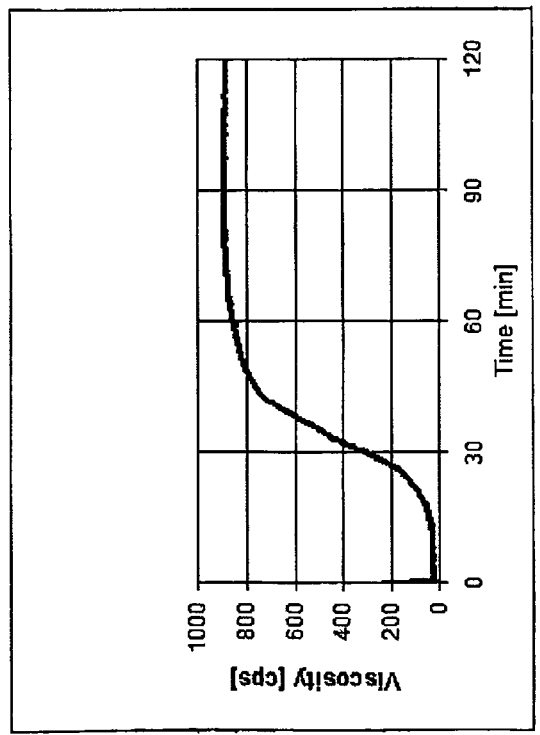
Figure 3:
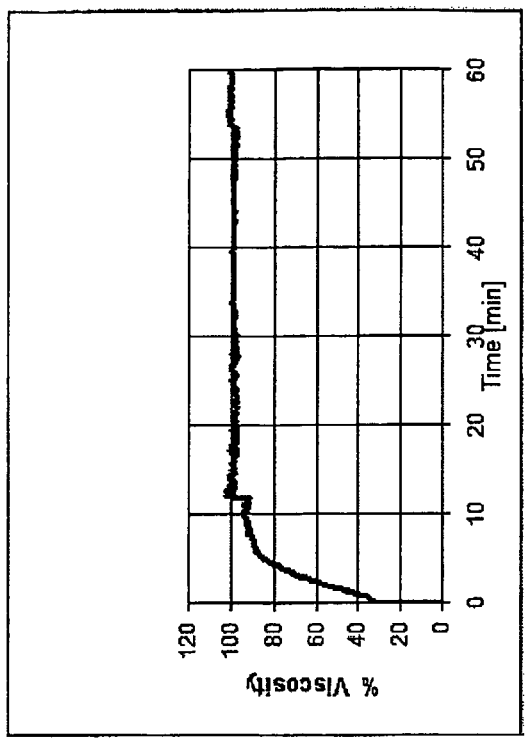
FIGS. 3 and 4 each contain plots of the viscosity in centipoise (cps) over time, as measured using a Haake Model VT501 viscometer, as well as plots of the percentage viscosity at given time based on the final viscosity of Comparative Example 2.
Figure 3:
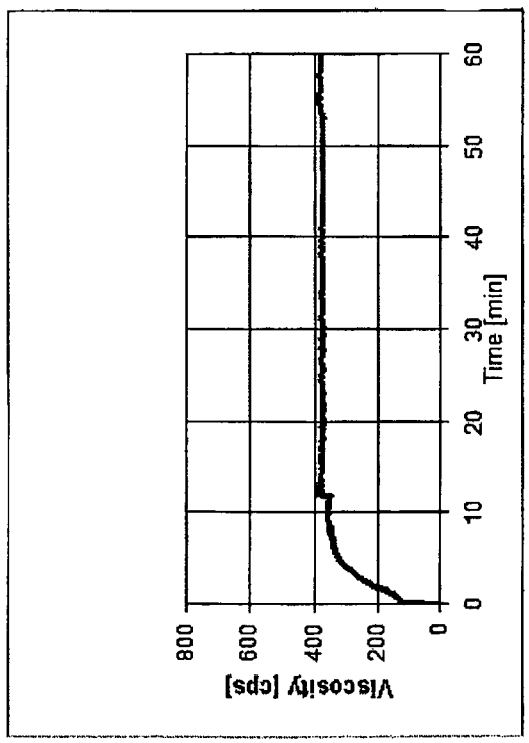
Figure 4:
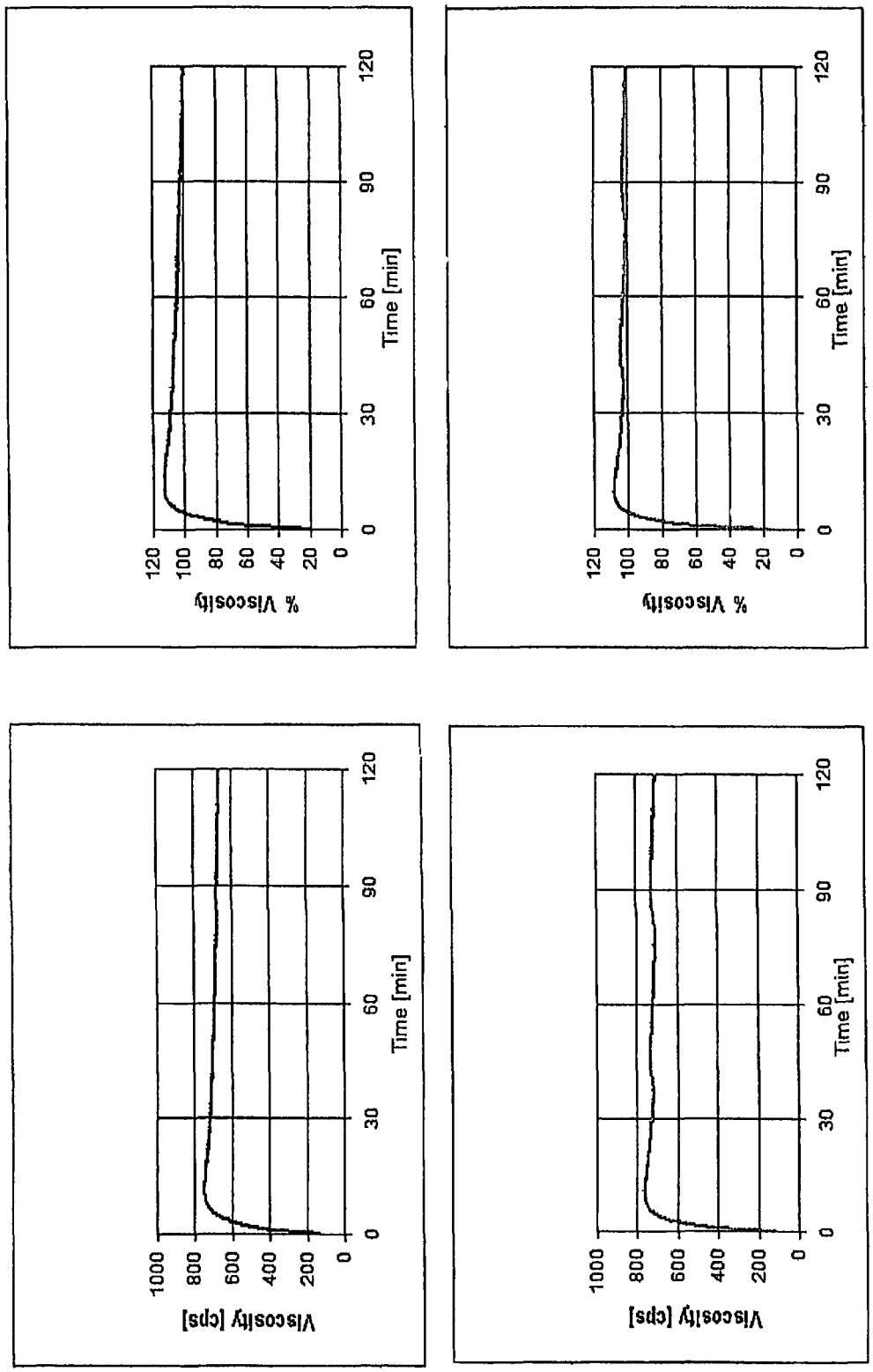
Figure 5:
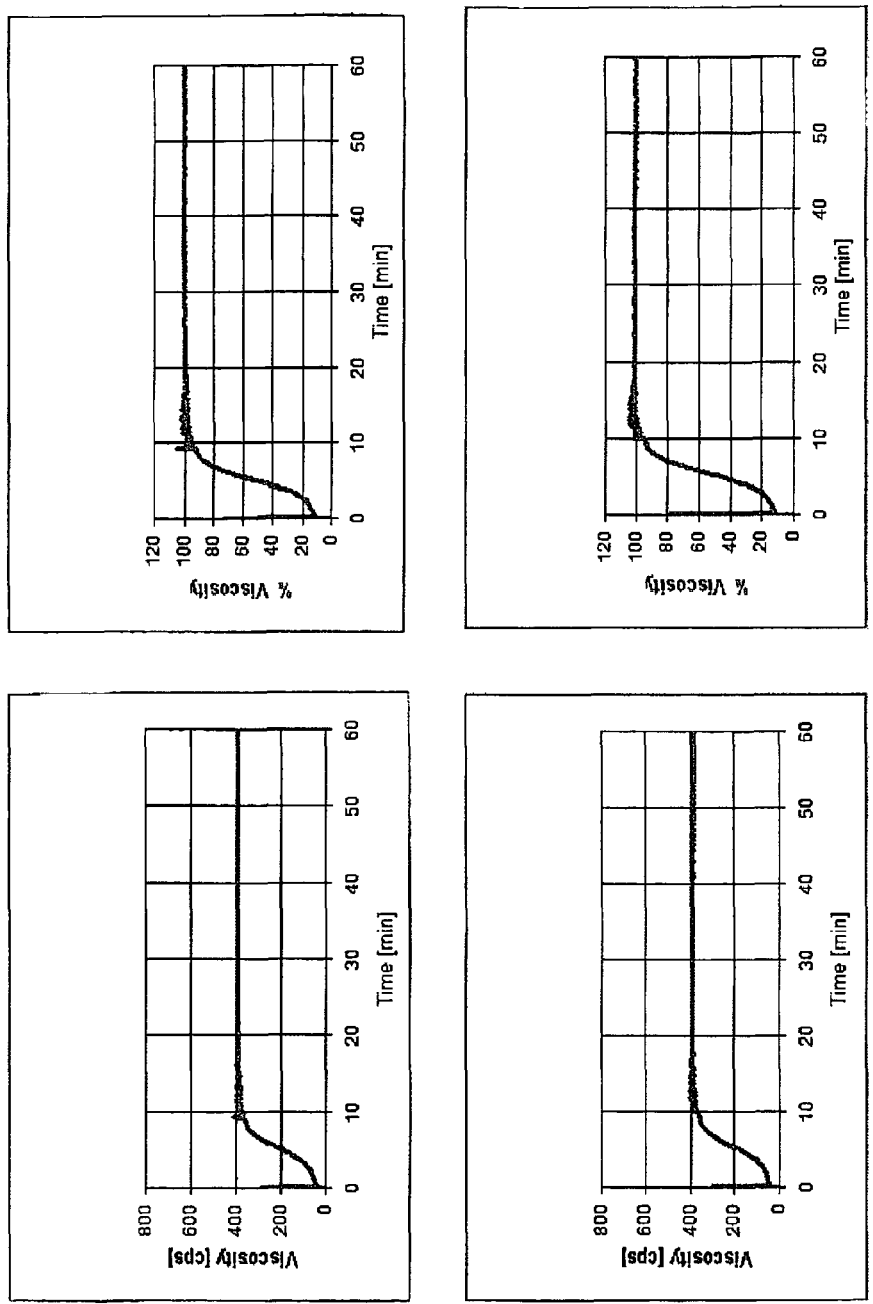
FIGS. 5 and 6 each contain plots of the viscosity in centipoise (cps) over time, as measured using a Haake Model VT501 viscometer, as well as plots of the percentage viscosity at given time based on the final viscosity of Example 1. Both FIGS. 5 and 6 contain duplicate tests.
Figure 6:
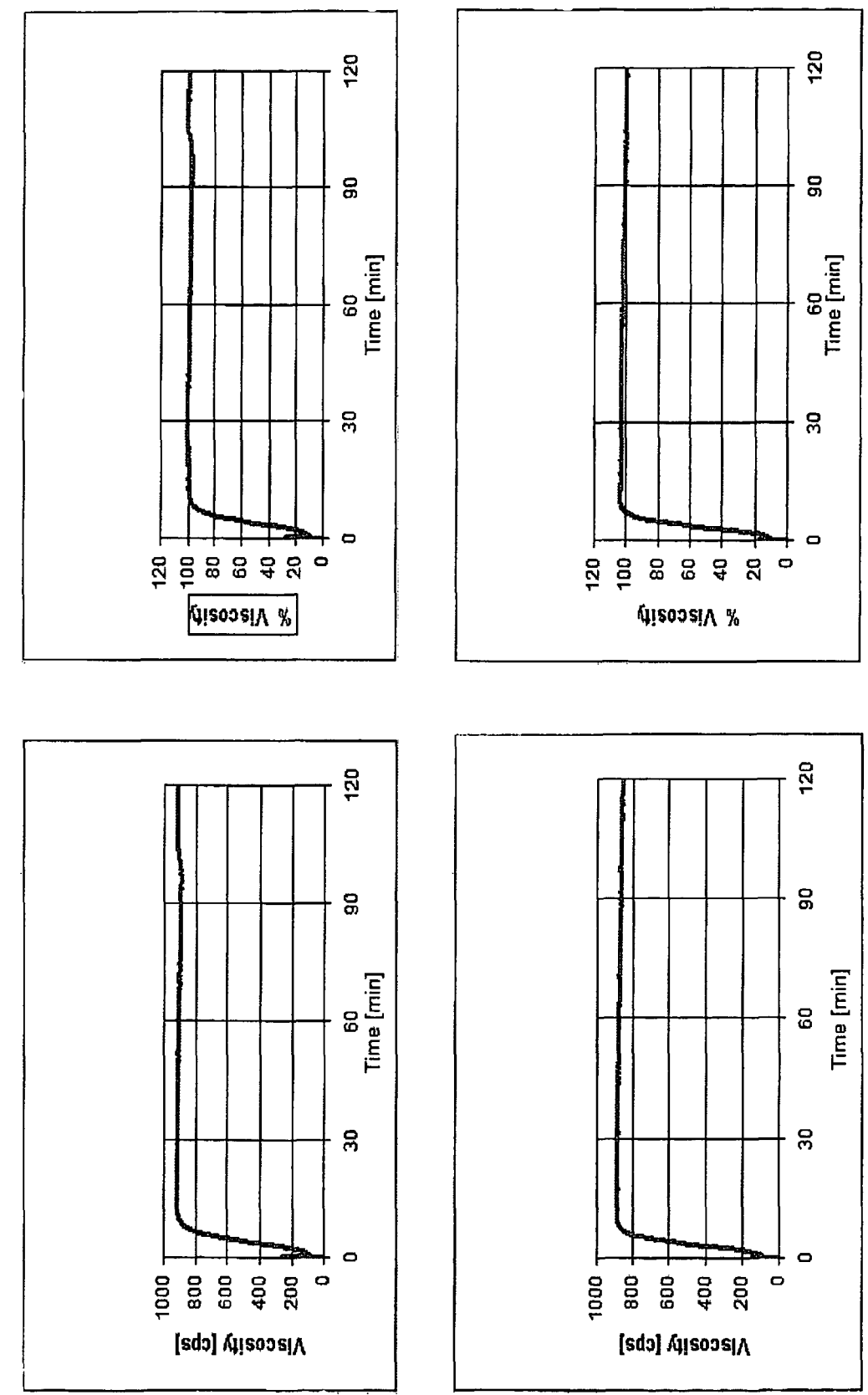

Other HEC samples (Natrosol® 250HHR CS HEC, Natrosol® 250HX Pharm HEC, and Natrosol® 250HHX Pharm HEC, all available from Hercules Incorporated) were included as comparative examples. The dispersions were made of examples of the agglomerated HEC of use in the present invention as well as the comparative examples at 0.5% and at 1.0%, see Table 1. The dispersions were mixed either for one (1) hour or two (2) hours and viscosity was measured as a function of time, FIGS. 1 to 6. The plots provide viscosity with time as measured by Haake viscometer and also % viscosity at given time based on the final viscosity.

Comparative Example 1

Natrosol® 250HHR CS HEC (glyoxal treated):
The Comparative Example 1 took almost 80 minutes to reach 100% of its final viscosity, both at 0.5% and at 1.0%, see FIGS. 1 & 2. No pH adjustment was made during the hydration study.

Comparative Example 2

Natrosol® 250HX Pham HEC (glyoxal-free):
At 0.5% concentration, comparative example 2 took about 12 minutes to reach 100% of its final viscosity, FIG. 3. No lumping was observed at 0.5% concentration. It took about 30 minutes at 1.0% concentration to reach 100% of its final viscosity, see FIG. 4. However, most of the viscosity gain occurred in the first 5 minutes. The 1.0% solution experiment was run in duplicate. In the first experiment a momentary lumping was observed when polymer was first added to water.

Comparative Example 3

Natrosol® 250HHX Pharm HEC (glyoxal-free):
The sample was not tested at 0.5% level. At 1.0%, it went-off the scale and the test was aborted.

Example 1

Natrosol® 250HHX-GF HEC (glyoxal-free), HEC agglomerated with 5% of a low viscosity HEC aqueous solution (Natrosol® L HEC available from Hercules Incorporated) in a fluid bed dryer.

Both 0.5% and 1.0% solution test were run in duplicate. It took about 10 minutes to reach 100% of its final viscosity at 0.5%, and less than 30 minutes at 1.0%. No lumping was observed, see FIGS. 5 & 6.

TABLE 1

Hydration Curves Measured with a Haake Viscometer for Example 1 and Comparative Examples 1-3

| Sample | Concentration in DI water, by weight (%) | Time (hrs.) | Figure | Comments |
|---|---|---|---|---|
| Comp. Ex. 1 | 1.00 | 1 | 2 | No lumping |
| Comp. Ex. 1 | 0.50 | 2 | 1 | No lumping |

TABLE 1-continued

Hydration Curves Measured with a Haake Viscometer
for Example 1 and Comparative Examples 1-3

| Sample | Concentration in DI water, by weight (%) | Time (hrs.) | Figure | Comments |
|---|---|---|---|---|
| Comp. Ex. 2 | 1.00 | 2 | 4 | In run #1, lumping initially but broke up quickly. Test run in duplicate. |
| Comp. Ex. 2 | 0.50 | 1 | 3 | No lumping |
| Comp. Ex. 3 | 1.00 | 2 | — | No lumping, off-scale, test aborted |
| Comp. Ex. 3 | 0.50 | 2 | — | No lumping |
| Ex. 1 | 1.00 | 2 | 6 | No lumping |
| Ex. 1 | 0.50 | 1 | 5 | No lumping |

Dispersion Properties with Propeller Blade Mixer

Solutions of the following polymers were prepared at 1.0% concentrations:

Comparative Example 4 (Natrosol® 250HX Pharm HEC);

Comparative Example 5 (Natrosol® 250HHX Pharm HEC); and

Example 2 (Natrosol® HHX-GF HEC).

The solutions were prepared in an 237 ml (8 oz) jar, two propeller blades at 450 rpm, with deionized water and under ambient temperature conditions.

No lumping was observed when Example 2 (Natrosol® HHX-GF HEC agglomerated with 5% of a low viscosity HEC aqueous solution (Natrosol® L hydroxyethyl cellulose available from Hercules Incorporated) in a fluid bed dryer) was first added to the deionized water.

Severe large lumping occurred with Comparative Example 4 (Natrosol® 250HX Pharm HEC, available from Hercules Incorporated.) The lump did not dissolve even after two (2) hours of mixing.

Severe small lumping occurred initially when Comparative Example 5 (Natrosol® 250HHX Pharm HEC, available from Hercules Incorporated) was added to deionized water, but then the material dissolved in less than a minute.

Other Physical Observations

Comparative Example 4 (Natrosol® 250HX Pharm HEC);
—Fine powder, lumpy (not free-flowing) in its container;
Comparative Example 5 (Natrosol® 250HHX Pharm HEC)—Fine granular material, no caking, dry free-flowing; and
Example 2 (Natrosol® HHX-GF HEC)—Coarse granular, dry free-flowing.

The composition of agglomerated hydroxyethylcellulose of use in this invention—agglomerated HEC, Natrosol® 250HHX-GF—provided excellent dispersion & dissolution without the lumping issue experienced by Comparative Examples 4 & 5, the Pharm grade products.

Experimental Procedure:

The materials tested were:
(Example 3), Dispersible Natrosol® 250HHX-GF HEC agglomerated with 5% of a low viscosity HEC aqueous solution (Natrosol® L hydroxyethyl cellulose available from Hercules Incorporated) in a fluid bed dryer;

(Comparative Example 4) Natrosol® 250HX-Pharm HEC;

(Comparative Example 5) Natrosol® 250HHX-Pharm HEC; and (Comparative Example 1) Natrosol® 250HHR-CS HEC.

The moisture content of each polymer was determined using a Sartorius Model MA-30 moisture balance @ 105° C.:

(Example 3) Dispersible Natrosol 250HHX-GF, 1.68% moisture;

(Comparative Example 4) Natrosol® 250HX-Pharm HEC, 3.43% moisture;

(Comparative Example 4) Natrosol® 250HX-Pharm HEC, 3.88% moisture;

(Comparative Example 5) Natrosol® 250HHX-Pharm HEC, 3.26% moisture; and (Comparative Example 1) Natrosol®250HHR-CS HEC, 4.61% moisture.

The weight of polymer in each formulation was adjusted for its moisture content.

The hydration tests were run on a Haake Model VT-501 Viscometer, equipped with an FL10 sensor. Rotation speed was 300 rpm. The solution batch size was 400 g. The measurement program was divided into eight time segments of varying length; during each segment 50 readings were taken. In these tests the following programs were used:

For one hour tests: −5 minutes/5 minutes/5 minutes/5 minutes/10 minutes/10 minutes/10 minutes/10 minutes; for a total of one hour.

For two hour tests: −5 minutes/5 minutes/10 minutes/20 minutes/20 minutes/20 minutes/20 minutes/20 minutes; for a total of two hours.

(In the first segment, −5 minutes was specified so that the sensor rotates at the specified speed immediately rather than ramping up to speed over the time segment).

After setting up the parameters of the Haake program, the water was charged to a 500 ml jacketed beaker maintained at 25° C. from a circulating water bath. The sensor was lowered into the beaker to about 0.6-1.3 cm (¼"-½") from the bottom of the beaker, and located slightly off-center to prevent the dry powder from accumulating on the sensor shaft. The sensor rotation was started and the polymer was added quickly to the vortex. The sensor was then centered in the beaker. The program was run until the prescribed end time.

The test solution charges were as follows:

|  | Sample | % solids |  | Average | % Moist. |
|---|---|---|---|---|---|
| Natrosol ® 250 HHX-GF HEC | Example 3 | 98.35 | 98.3 | 98.325 | 1.68 |
| Natrosol ® 250 HX-Pharm HEC | Comp Ex. 4 | 96.52 | 96.63 | 96.575 | 3.43 |
| Natrosol ® 250HHX-Pharm HEC | Comp Ex. 5 | 96.03 | 96.21 | 96.12 | 3.88 |
| Natrosol ® 250HHX-Pharm HEC | Comp Ex. 5 | 96.85 | 96.63 | 96.74 | 3.26 |
| Natrosol ® 250HHR-CS HEC | Comp Ex. 1 | 95.31 | 95.48 | 95.395 | 4.61 |

| 1.00% concentration | 13A | 13 B | 13 C | 13D | 13E |
|---|---|---|---|---|---|
| Deionized water | 395.932 | 395.858 | 395.839 | 395.865 | 395.807 |
| Example 3 | 4.068 |  |  |  |  |
| Comp Ex. 4 |  | 4.142 |  |  |  |
| Comp Ex. 4 |  |  | 4.161 |  |  |
| Comp Ex. 5 |  |  |  | 4.135 |  |
| Comp Ex. 1 |  |  |  |  | 4.193 |
|  | 400.00 | 400.00 | 400.00 | 400.00 | 400.00 |

| 0.50% concentration | 13 F | 13 G | 13 H | 13 I | 13J |
|---|---|---|---|---|---|
| Deionized water | 397.966 | 397.929 | 397.919 | 397.933 | 397.903 |
| Example 3 | 2.034 |  |  |  |  |
| Comp Ex. 4 |  | 2.071 |  |  |  |
| Comp Ex. 4 |  |  | 2.081 |  |  |
| Comp Ex. 5 |  |  |  | 2.067 |  |
| Comp Ex. 1 |  |  |  |  | 2.097 |
|  | 400.00 | 400.00 | 400.00 | 400.00 | 400.00 |

Example 4

Hair Conditioner

An example of a hair conditioner was produced using the agglomerated HEC described in the preceding examples.
Ingredients:
  Agglomerated HEC of Example 3
  Comparative Example 1
  Comparative Example 5
  Cetyl alcohol: Crodacol C95NF from Croda
  Potassium Chloride: VWR
  Isopropyl myristate: Stepan IPM from Stepan
  Preservative: Germaben II from ISP A hair conditioner was produced with the following proportions:

| 187.5 g | Deionized Water |
| 2.50 g | Agglomerated HEC of Example 3 |
| 4.00 g | Cetyl alcohol |
| 1.00 g | Potassium Chloride |
| 4.00 g | Isopropyl myristate |
| 1.00 g | Preservative |

The agglomerated HEC of Example 3 was added into vortex of water and mixed until fully dissolved. Next, the solution was heated to 65° C. in a water-bath. Next cetyl alcohol was added and mixed until homogeneously mixed. The solution was then cooled to 50° C. and potassium chloride was added while mixing. Next, isopropyl myristate was added to the solution and mixed until homogeneous, producing a conditioner.

The pH of the conditioner was adjusted between 5.25 to 5.5 with 5% citric acid and/or 5% sodium hydroxide solution. The final conditioner product was observed to be smooth and free of any gels. The final viscosity of the conditioner product was 9,600 cps.

The Example 4 conditioner product was repeated by replacing agglomerated HEC of Example 3 with Comparative Example 5. It was observed that the final comparative conditioner product had few gels. The final comparative conditioner product viscosity was not measured due to gels.

The comparative conditioner product was repeated by replacing agglomerated HEC of Example 3 with Comparative Example 1. The conditioner had few small gels. The final comparative conditioner product viscosity was 9,000 cps.

Example 5

Skin Lotion

An example of a skin lotion was produced using the agglomerated HEC described in the preceding examples.
Ingredients:
  Glycerin: USP grade from Spectrum
  Glycol stearate: Kessco® EGMS from Stepan
  Stearic acid: Industrene® 5016 from Witco Corp
  Mineral oil: Drakeol® 7, Penreco
  Acetylated lanolin: Lipolan® 98, Lipo Chemicals
  Cetyl alcohol: Crodacol® C95, Croda Inc
  Triethanol amine; 99% Acros
  Agglomerated HEC of Example 3 (Hydroxyethyl cellulose—Natrosol® 250 HH-GF HEC, available from Hercules Incorporated)
  Comparative Example 1
  Comparative Example 5
  Preservative: Germaben® II from ISP Corp A skin lotion was produced with the following proportions:

| | Part I | |
|---|---|---|
| 156.5 g | Deionized water | |
| 4.0 g | Glycerin | |
| | Part II | |
| 5.5 g | Glycol stearate | |
| 5.0 g | Stearic acid | |
| 4.0 g | Mineral oil | |
| 1.0 g | Acetylated lanolin | |
| 0.5 g | Cetyl alcohol | |
| | Part III | |
| 20.0 g | Deionized water | |
| 1.0 g | Triethanol amine | |
| | Part IV | |
| 1.0 g | Agglomerated HEC of Example 3 | |
| | Part IV | |
| 1.5 g | Preservative | |

A skin lotion was produced using the following procedure: The ingredients of Part II were mixed in a beaker and heated to 80° C. In a separate beaker, the ingredients of Part I were mixed and heated to 80° C. Next, the mixture of Part I was added to the mixture of Part II while mixing. In a separate third beaker, ingredients of Part III were mixed and then added to the mixture of Part I and II while mixing at 80° C. Next, the agglomerated HEC of Example 3 was added to the vortex of the mixture consisting of Part I, II and III. Mixing was continued for about 10 minutes and then the mixture was permitted to cool to 40° C. When the mixture cooled to 40° C., the pH of the emulsion was adjusted to 6.0 to 6.5. Next, the preservative was added and the mixture was permitted to cool further to room temperature while mixing resulting in a final skin lotion.

The final skin lotion was observed to be smooth and free of any gels. The final viscosity of the skin lotion was 13400 cps.

For comparative purposes, the procedure for producing the skin lotion of Example 5 was repeated by replacing the agglomerated HEC of Example 3 with the glyoxal treated HEC of Comparative Example 5. Some lumping occurred initially when the glyoxal treated HEC of Comparative Example 5 was added to the mixture consisting of Part I, II and III, and the glyoxal treated HEC of Comparative Example 5 was observed to take a longer time to solublize when compared to the agglomerated HEC of Example 3 of use in the present invention. The resultant comparative skin lotion was free of any gels. The final viscosity of the comparative skin lotion was 18,600 cps.

For comparative purposes, the procedure for producing the skin lotion of Example 5 was again repeated by replacing the agglomerated HEC of Example 3 with the glyoxal treated HEC of Comparative Example 1. In the comparative skin lotion, it was observed that a sufficient amount of heat was essential to dissolve the glyoxal treated HEC of Comparative Example 1 otherwise a longer mixing time was required when compared to the agglomerated HEC of Example 3. The resultant comparative skin lotion was observed to be smooth. The final viscosity of the comparative skin lotion was 10,600 cps.

Example 6

Conditioning Shampoo

An example of a conditioning shampoo was produced using the agglomerated HEC described in the preceding examples.

Ingredients:
  Sodium laureth sulfate 2EO (SLES): Texapon® N70NA from Cognis
  Cocoamidopropyl betaine (CAPB): Velvetex® BA35 from Cognis
  Coconut Fatty acid diethanolamide: Comperlan® COD from Cognis
  Agglomerated HEC of Example 3 (Hydroxyethyl cellulose—Natrosol® 250 HH-GF HEC, available from Hercules Incorporated)
  Comparative Example 1
  Comparative Example 5
  Cationic guar: N-Hance® 3205, Cationic guar from Aqualon
  Silicone emulsion: Dow Corning 1784 from Dow Corning
  Preservative: DMDM Hydantoin, Glydant® from Lonza A conditioning shampoo was produced with the following proportions:

| | |
|---|---|
| 146.36 g | Deionized Water |
| 34.24 g | Sodium laureth sulfate 2EO (SLES) |
| 6.00 g | Cocoamidopropyl betaine (CAPB) |
| 4.00 g | Coconut Fatty acid diethanolamide |
| 2.00 g | Agglomerated HEC of Example 3 |
| 0.40 g | Cationic guar |
| 6.00 g | Silicone emulsion |
| 1.00 g | Preservative |

A conditioning shampoo was produced using the following procedure: Cationic guar was added to vortex of water. The cationic guar was mixed for 30 minutes. Next, agglomerated HEC of Example 3 was added to the cationic guar mixture and mixed for an additional 30 minutes. Next, the remaining ingredients from the above list were added to the mixture in the order listed. Between each subsequent addition, the mixture was allowed to mix for until it appeared to be homogeneous. A longer mixing time was required after the addition of sodium laureth sulfate. The pH of the final conditioning shampoo was adjusted to 5.0 to 5.5 with citric acid. The final conditioning shampoo was observed to be smooth, opaque and free of any gels. The final conditioning shampoo had a viscosity of about 8500 cps.

For comparative purposes, the procedure for producing the conditioning shampoo of Example 6 was repeated by replacing the agglomerated HEC of Example 3 with the glyoxal treated HEC of Comparative Example 5. The final comparative conditioning shampoo had large few gels. The viscosity of the final comparative conditioning shampoo 15,800 cps.

For comparative purposes, the procedure for producing the conditioning shampoo of Example 6 was again repeated by replacing the agglomerated HEC of Example 3 with the glyoxal treated HEC of Comparative Example 1. The Comparative Example 1 HEC polymer did not dissolve initially as the agglomerated HEC of Example 3 did. The final comparative conditioning shampoo was observed to be stable, opaque and having a viscosity of 7500 cps.

Example 7

Shampoo

An example of a shampoo was produced using the agglomerated HEC described in the preceding examples.

Ingredients:
- Sodium laureth sulfate 3EO (SLES): Steol® CS330 from Stepan
- Cocoamidopropyl betaine (CAPB): Amphosol® CA from Stepan
- Sodium lauroyl sacosinate: Crodasinic® LS-30 from Croda Corp
- Agglomerated HEC of Example 3 (Hydroxyethyl cellulose—Natrosol® 250 HH-GF HEC, available from Hercules Incorporated)
- Comparative Example 1
- Comparative Example 5
- Preservative: Kathon® CG from Rohm & Haas A shampoo was produced with the following proportions:

| | |
|---|---|
| 126.06 g | Deionized water |
| 39.20 g | Sodium laureth sulfate 3EO (SLES) |
| 13.34 g | Cocoamidopropyl betaine (CAPB) |
| 19.20 g | Sodium lauroyl sacosinate |
| 2.00 g | Agglomerated HEC of Example 3 |
| 00.20 g | Preservative |

A shampoo was produced using the following procedure: The ingredients were added in the order listed to vortex of water. After each addition, the solution was mixed for homogeneous mixing of ingredients. The final shampoo was smooth, slightly hazy and free of any gels. The final shampoo viscosity was about 6,000 cps.

For comparative purposes, the procedure for producing the shampoo of Example 7 was repeated by replacing the agglomerated HEC of Example 3 with the glyoxal treated HEC of Comparative Example 5. The glyoxal treated HEC of Comparative Example 5 took longer time to dissolve than the agglomerated HEC of Example 3 with some lumping initially observed. The final comparative shampoo was smooth, slightly hazy and free of any gels. The final viscosity of the comparative shampoo was about 6,000 cps.

For comparative purposes, the procedure for producing the shampoo of Example 7 was again repeated by replacing the agglomerated HEC of Example 3 with the glyoxal treated HEC of Comparative Example 1. The glyoxal treated HEC of Comparative Example 1 did not dissolve initially as the agglomerated HEC of Example 3 did. The final comparative shampoo was observed to be slightly grainy in texture, slightly hazy and free of any gels. The final viscosity of the comparative shampoo was about 5,900 cps.

Example 8

Body Wash

An example of a Body Wash was produced using the agglomerated HEC described in the preceding examples.

Ingredients:
- Agglomerated HEC of Example 3 (Hydroxyethyl cellulose—Natrosol® 250 HH-GF HEC, available from Hercules Incorporated)
- Comparative Example 1
- Comparative Example 5
- Sodium laureth Sulfate (SLES): Steol® CS330 from Stepan
- Cocoamidopropyl betaine (CAPB): Amphosol® CA from Stepan
- Cationic guar: AquaCat® CG available from Hercules Incorporated
- Methyl Gluceth 20: Glucam® E20 from Noveon
- Preservative: Glydant® from Lonza A Body Wash was produced with the following proportions:

| | |
|---|---|
| 102.00 g | Deionized water |
| 2.00 g | Agglomerated HEC of Example 3 |
| 84.00 g | Sodium laureth Sulfate (SLES) |
| 6.00 g | Cocoamidopropyl betaine (CAPB) |
| 4.0 g | Cationic guar |
| 1.0 g | Methyl Gluceth 20 |
| 1.00 g | Preservative |

A Body Wash was produced using the following procedure: The agglomerated HEC of Example 3 was added to the vortex of water created by the stirrer. Next, the remaining ingredients were added in the order listed above to vortex of solution allowing time for homogeneous mixing between each subsequent addition. The final Body Wash pH was adjusted 5.0 to 6.0 with citric acid. The final Body Wash was observed to be smooth, slightly hazy and free of any gels. The final Body Wash viscosity was about 6,200 cps.

For comparative purposes, the procedure for producing the Body Wash of Example 8 was repeated by replacing the agglomerated HEC of Example 3 with the glyoxal treated HEC of Comparative Example 5. The glyoxal treated HEC of Comparative Example 5 did not fully dissolve initially. The final comparative Body Wash was observed to be smooth, slightly hazy and free of any gels. The final comparative Body Wash viscosity was about 6,800 cps.

For comparative purposes, the procedure for producing Body Wash of Example 8 was again repeated by replacing the agglomerated HEC of Example 3 with the glyoxal treated HEC of Comparative Example 1. The glyoxal treated HEC of Comparative Example 1 did not dissolve initially as the agglomerated HEC of Example 3 did. The final comparative Body Wash was observed to be slightly grainy, slightly hazy and free of any gels. The final comparative Body Wash viscosity was about 5,000 cps.

Example 9

Shampoo (with Post Addition of HEC)

An example of a shampoo was produced using the agglomerated HEC described in the preceding examples. This example is was produced to determine whether the agglomerated HEC of the present invention would allow post addition of HEC in to the shampoo to make a stable product.

Ingredients:
- Agglomerated HEC of Example 3 (Hydroxyethyl cellulose—Natrosol® 250 HH-GF HEC, available from Hercules Incorporated)
- Comparative Example 1
- Comparative Example 5
- Sodium laureth Sulfate (SLES): Steol® CS330 from Stepan
- Cocoamidopropyl betaine (CAPB): Amphosol® CA from Stepan
- Cationic guar: AquaCat® CG guar from Hercules Incorporated
- Methyl Gluceth 20: Glucam® E20 from Noveon
- Preservative: Glydant®, Lonza A shampoo was produced with the following proportions:

| | | |
|---|---|---|
| 102.00 | | Deionized water |
| 84.00 | g | Sodium laureth Sulfate (SLES) |
| 6.00 | g | Cocoamidopropyl betaine (CAPB) |
| 4.0 | g | Cationic guar |
| 1.0 | g | Methyl Gluceth 20 |
| 2.00 | g | Agglomerated HEC of Example 3 |
| 1.00 | g | Preservative |

The ingredients were added in the order listed to the vortex of water created by the stirrer allowing time for homogeneous mixing between each addition. The final shampoo pH was adjusted 5.0 to 6.0 with citric acid. The final shampoo was observed to be smooth, slightly hazy and free of any gels. The viscosity of the final shampoo was about 6,100 cps.

For comparative purposes, the procedure for producing the shampoo of Example 9 was repeated by replacing the agglomerated HEC of Example 3 with the glyoxal treated HEC of Comparative Example 5. The glyoxal treated HEC of Comparative Example 5 did not fully dissolve. The final comparative shampoo had gel layer. The viscosity of the final comparative shampoo was about 7,200 cps.

For comparative purposes, the procedure for producing the shampoo of Example 9 was again repeated by replacing the agglomerated HEC of Example 3 with the glyoxal treated HEC of Comparative Example 1. The glyoxal treated HEC of Comparative Example 1 did not dissolve. The final comparative shampoo had gel layer. The viscosity of the final comparative shampoo was not measured due to the gel layer.

This example demonstrates that the agglomerated HEC of Example 3 may be added into a shampoo to make a stable shampoo product while the comparative glyoxal treated HECs of Comparative Examples 1 & 5 do not result in stable shampoo products when post added to a shampoo product.

Example 10

Floor Cleaner

An example of a Floor Cleaner was produced using the agglomerated HEC described in the preceding examples.
Ingredients:
Soybean oil, methyl ester: Steposol® SB-W from Stepan
D-limonene: Florida Chemical Co.
Fatty alkanomide: Ninol® 11-CM from Stepan
Triethanol amine: Arcos
Propylene glycol
Agglomerated HEC of Example 3 (Hydroxyethyl cellulose—Natrosol® 250 HH-GF HEC, available from Hercules Incorporated)
Preservative: DMDM Hydantoin, Glydant® from Lonza
A Floor Cleaner was produced with the following proportions:

| Part I | | |
|---|---|---|
| 7.95 | g | Soybean oil, methyl ester |
| 1.98 | g | D-limonene |
| 68.41 | g | Fatty alkanomide |
| 3.42 | g | Triethanol amine |
| 6.08 | g | Deionized water |
| 6.08 | g | Propylene glycol |

| Part II | | |
|---|---|---|
| 238.80 | g | Deionized water |
| 1.50 | g | Agglomerated HEC of Example 3 ( |
| 1.20 | g | Preservative |

| Part III | | |
|---|---|---|
| 60.00 | g | Part I |
| 241.5 | g | Part II |

A Floor Cleaner was produced using the following procedure: Ingredients of Part I were combined in the order listed above and mixed about 10 minutes in between each addition. Then deionized water was added very slowly to the mixture and the mixture was allowed to mix for an about an hour. The mixing speed was adjusted to insure full mixing of the ingredients. Finally, propylene glycol was added and the resulting mixture was mixed about 30 minutes, until it appeared to be homogeneous. This resulted in a Floor Cleaner concentrate of Part I.

To produce Part II, the Agglomerated HEC of Example 3 was added while mixing the deionized water. The solution was mixed for about 15 minutes and then the preservative DMDM Hydantoin was added to the solution. This mixture was mixed for approximately 5 minutes.

Part III (Combined Part 1 and Part 2). The floor cleaner concentrate (Part I) was added to the Agglomerated HEC of Example 3 solution (Part II). The solution was mixed for about 15 minutes to produce the final Floor Cleaner.

The final viscosity of the Floor Cleaner was 4760 cps and its pH was 9.16. The finished Floor Cleaner appeared clear yellow.

A control example of the Floor Cleaner of Example 10 was produced without the addition of the Agglomerated HEC of Example 3. This comparative Floor Cleaner material had a viscosity of only 350 cps.

Example 11

Dish Washing Liquid

An example of a Dish Washing Liquid was produced using the agglomerated HEC described in the preceding examples.
Ingredients:
Agglomerated HEC of Example 3 (Hydroxyethyl cellulose—Natrosol® 250 HH-GF HEC, available from Hercules Incorporated)
Ammonium laureth sulfate Steol® CA460 from Stepan
Sodium alphasulfo methyl C12-18 Ester (and) Disodium Alphasulpho C12-18 fatty acid salt: Alpha-Step MC-48 from Stepan
Cocamidopropyl betaine (CAPB): Amphosol CG from Stepan
Lauramine oxide: Ammonyx® from Stepan
Ethanol
Preservative: DMDM Hydantoin, Glydant® from Lonza
A Dish Washing Liquid was produced with the following proportions

| | | |
|---|---|---|
| 159.94 | g | Deionized water |
| 0.32 | g | Agglomerated HEC of Example 3 |
| 0.81 | g | Preservative |
| 80.85 | g | Ammonium laureth sulfate (Steol CA460, Stepan) |
| 26.10 | g | Sodium alphasulfo methyl C12-18 Ester (and) Disodium Alphasulpho C12-18 fatty acid salt |

| | |
|---|---|
| 12.99 g | Cocamidopropyl betaine (CAPB) |
| 12.99 g | Lauramine oxide |
| 6.00 g | Ethanol |

A Dish Washing Liquid was produced using the following procedure. Agglomerated HEC of Example 3 was added to deionized water while mixing. This solution was allowed to mix for about 15 minutes. Next, DMDM Hydantoin was added to the solution and this solution was permitted to mix for approximately an additional 5 minutes. The rest of ingredients in the order they appear in the above list with continuous stirring. After each ingredient addition, the resultant solution was permitted to be mixed for about 10 minutes or until homogeneous, prior to the addition of the next ingredient. Upon completion, the pH of final Dish Washing Liquid was adjusted with citric acid to 7.6.

The final Dish Washing Liquid had a viscosity of 99 cps. Its pH was 7.55, and it had a clear appearance.

A control example of the Dish Washing Liquid of Example 11 was produced without the addition of the Agglomerated HEC of Example 3. This comparative Dish Washing Liquid material had a viscosity of only 30 cps, and it had a clear appearance.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed:

1. A consumer product comprising:
    a) a glyoxal-free agglomerated hydroxyethylcellulose composition,
    b) a consumer product active ingredient material, and
    c) water,
wherein the glyoxal-free agglomerated hydroxethylcellulose composition comprises spraying a particulate hydroxyethylcellulose with an aqueous solution of a low molecular weight hydroxyethylcellulose; wherein the consumer product is selected from the group consisting of pharmaceutical, personal care and household care applications, wherein the consumer product is not an oral care composition; and wherein the low molecular weight hydroxyethylcellulose has a lower molecular weight than the particulate hydroxyethylcellulose and exhibits a viscosity in a 2% aqueous solution of less than 350 cps.

2. The consumer product of claim 1, wherein the low molecular weight HEC exhibits a viscosity in a 2% aqueous solution of approximately 15 cps.

3. The consumer product of claim 1, wherein the consumer product comprises a hair conditioner.

4. The consumer product of claim 1, wherein the glyoxal-free agglomerated hydroxyethylcellulose composition has a particle size range of 400-800 microns.

5. The consumer product of claim 1, wherein the glyoxal-free particulate hydroxyethylcellulose has a 1% aqueous viscosity of 1500 to 2500 cps at 25° C.

6. The consumer product of claim 1, wherein the consumer product comprises a skin lotion.

7. The consumer product of claim 1, wherein the consumer product comprises a shampoo.

8. The consumer product of claim 1, wherein the consumer product comprises a conditioning shampoo.

9. The consumer product of claim 1, wherein the consumer product comprises a body wash.

10. The consumer product of claim 1, wherein the consumer product comprises a floor cleaner.

11. The consumer product of claim 1, wherein the consumer product comprises a dish washing liquid.

\* \* \* \* \*